(12) United States Patent
Bacher et al.

(10) Patent No.: US 6,991,621 B2
(45) Date of Patent: Jan. 31, 2006

(54) MEDICAL INSTRUMENT FOR IRRIGATION AND/OR SUCTION

(75) Inventors: Uwe Bacher, Tuttlingen (DE); Horst Dittrich, Immendingen (DE)

(73) Assignee: Karl Storz GmbH & Co. KG, (DE)

( * ) Notice: Subject to any disclaimer, the term of this patent is extended or adjusted under 35 U.S.C. 154(b) by 0 days.

(21) Appl. No.: 10/348,441

(22) Filed: Jan. 21, 2003

(65) Prior Publication Data
US 2003/0139708 A1   Jul. 24, 2003

(30) Foreign Application Priority Data
Jan. 21, 2002   (EP) .................................. 02001463

(51) Int. Cl.
*A61M 5/00*   (2006.01)
(52) U.S. Cl. ................... 604/247; 604/167.01
(58) Field of Classification Search ............... 604/247, 604/110, 249, 167.01, 167.03, 167.05, 167.06, 604/246, 256, 254, 19, 32, 364
See application file for complete search history.

(56) References Cited

U.S. PATENT DOCUMENTS 1,334,870 A   3/1920 Lowry

| 5,030,199 | A | | 7/1991 | Barwick et al. ............... 600/29 |
|---|---|---|---|---|
| 5,306,122 | A | * | 4/1994 | Gebauer et al. ............ 417/383 |
| 5,312,373 | A | | 5/1994 | Freitas ........................ 604/249 |
| 5,827,234 | A | * | 10/1998 | Loos et al. .................. 604/236 |

FOREIGN PATENT DOCUMENTS

| DE | 28 00 607 | 10/1978 |
|---|---|---|
| DE | 200 11 409 | 11/2000 |
| FR | 2 646 771 | 11/1990 |
| GB | 1 346 057 | 2/1974 |

* cited by examiner

*Primary Examiner*—Kevin C. Sirmons
(74) *Attorney, Agent, or Firm*—St. Onge Steward Johnston & Reens LLC

(57) ABSTRACT

A medical instrument for irrigation and/or suction has an instrument body in which at least one flow channel is present for the passage of a fluid, at least one shut-off member for alternately shutting off the at least one flow channel, and an actuating member for actuating the shut-off member. The at least one shut-off member is a ball which, in a closure position, lies sealingly on a sealing edge of the flow channel so that it closes off the internal cross section of the flow channel, the ball being movable, between the closure position for closing the flow channel and a release position for freeing the flow channel, substantially in a direction transverse to the longitudinal direction of the flow channel, and the actuating member for moving the ball between the closure position and the release position being movable in a direction transverse to the flow channel.

12 Claims, 4 Drawing Sheets

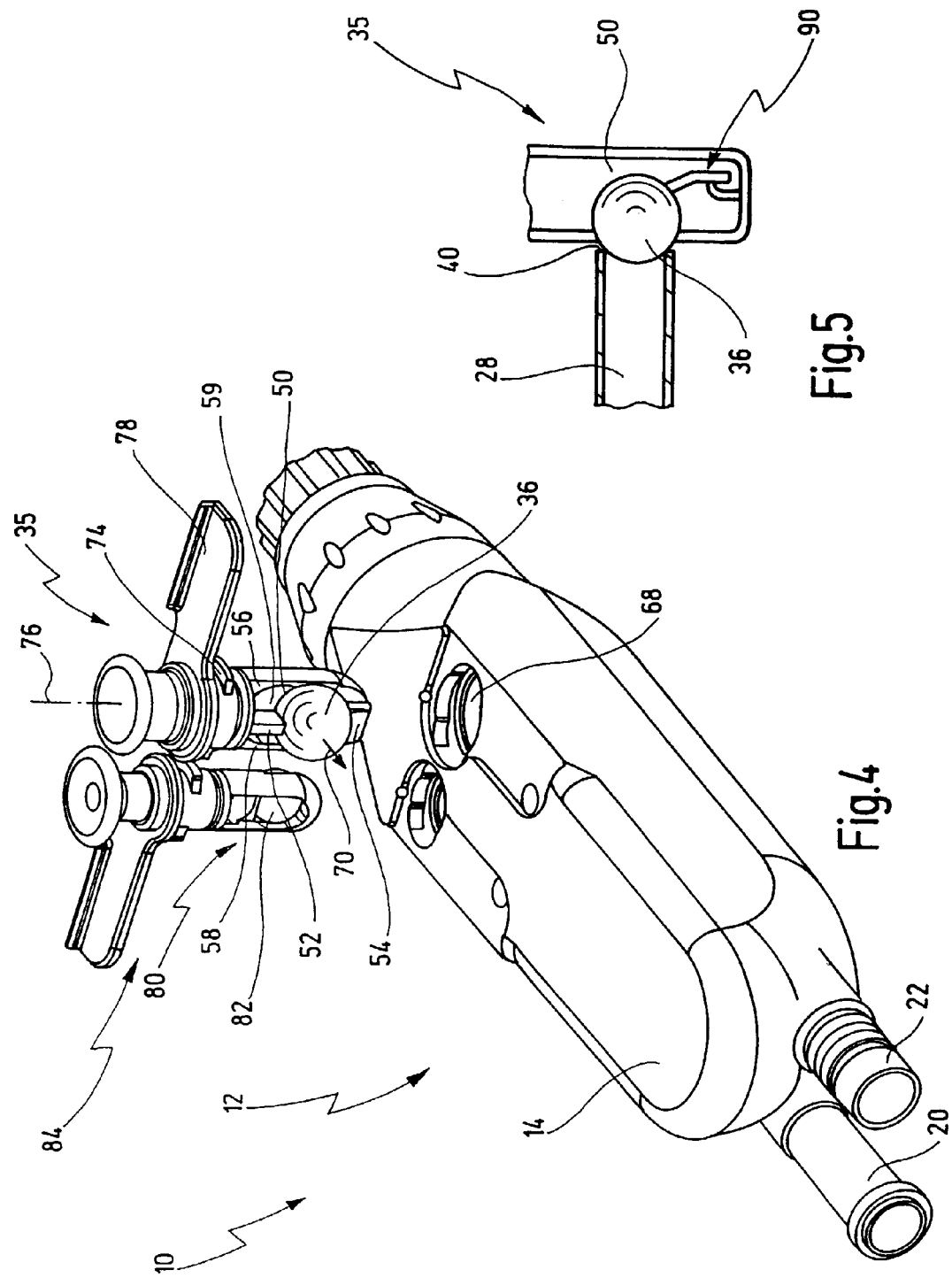

MEDICAL INSTRUMENT FOR IRRIGATION AND/OR SUCTION

BACKGROUND OF THE INVENTION

The invention relates to a medical instrument for irrigation and/or suction, with an instrument body in which at least one flow channel is present for the passage of a fluid, and with at least one shut-off member for alternately shutting off the at least one flow channel, and with an actuating member for actuating the shut-off member.

An instrument of this kind is known from the German utility model DE 200 11 409 U1.

Such a suction and/or irrigation instrument is used in surgery, in particular in minimally invasive surgery, in order to irrigate the operating site with irrigation fluid during a surgical intervention and/or to aspirate fluid, for example the introduced irrigation fluid, blood and tissue remnants from the operating site.

The aforementioned known instrument is suitable both for irrigation and for suction. Although the present invention is preferably described taking the example of an instrument for irrigation and suction, the present invention is not however restricted to this, and instead it also includes those instruments which can be used either only for irrigation or only for suction.

Likewise, the term "instrument body" within the meaning of the present invention is to be understood in its general sense and can include the shaft of such an instrument and/or the handgrip of such an instrument.

In accordance with its dual function, the known instrument for irrigation and suction has two flow channels in the instrument body, one flow channel representing the irrigation channel and the other flow channel representing the suction channel. The irrigation channel and the suction channel are separate from one another.

At the proximal end of the instrument, the known instrument has an attachment piece for attaching a suction tube and an attachment piece for attaching an irrigation tube. The suction tube and the irrigation tube are connected to a suction and irrigation source, a suitable underpressure being established on the suction tube and directed from the distal end to the proximal end of the instrument, and irrigation fluid being conveyed through the irrigation tube from proximal to distal. The suction underpressure and the irrigation fluid are preferably permanently present on the instrument after the suction and irrigation source has-been switched on.

In order to be able to interrupt the suction stream and/or the irrigation stream, the known instrument is provided with a shut-off member for alternately shutting off or free the respective flow channel, and the shut-off member can be actuated by the operator via an actuating member in the form of a slide. In the known instrument, the shut-off member has a movable plate connected to the slide, provided with recesses and arranged to slide on an immovable plate in the instrument body. The immovable plate is designed with openings which communicate with the at least one flow channel. By actuating the slide, the movable plate is displaced relative to the immovable plate, so that the recesses of the movable plate and the openings of the immovable plate move into or out of coincidence. In this way, the suction stream or the irrigation stream can be freed, or the suction channel and/or the irrigation channel can be shut off. The movable plate and the immovable plate lie directly on one another, their surfaces touching one another, both plates being made of a ceramic material in the area of their touching surfaces.

A disadvantage of this known construction is that ceramic plates of this kind are very expensive to produce. Moreover, when there are high suction or irrigation pressures, these kinds of ceramic plates lying on one another require high locking forces in order to achieve the necessary sealing action. These high locking forces in turn generate a high level of friction between the movable and the immovable plate, resulting in high operating forces upon actuation of the actuating member.

The object of the invention therefore is to develop an instrument of the type specified in the introduction in such a way that the aforementioned disadvantages are avoided, i.e. a good sealing action of the shut-off member is achieved, and yet the operating forces for actuating the shut-off member are kept as low as possible.

SUMMARY OF THE INVENTION

According to the invention, a medical instrument is provided, comprising:
an instrument body in which at least one flow channel is present having an internal cross section for the passage of a fluid, said flow channel extending in a longitudinal direction;
at least one shut-off member configured as a ball which is movable between a closure position where said ball lies sealingly on a sealing edge of said at least one flow channel so that it closes off said internal cross section of said flow channel, and a release position where said ball frees said flow channel, said ball being elastic in shape;
at least one actuating member for moving said ball between said closure position and said release position, said actuating member having a press-button for operating said actuating member;
wherein said ball and said actuating member are movable between said closure position and said release position substantially in a direction transverse to said longitudinal direction of said flow channel, and wherein said actuating member can be removed from said instrument body together with said ball.

Accordingly, the instrument according to the invention has a kind of ball valve. The ball has an external diameter which is greater than the internal diameter of the at least one flow channel which the ball in the closure position is intended to close. The ball thus lies sealingly on the sealing edge of the flow channel in the form of a line of a circle or a ring sector, as a result of which, in contrast to the ceramic plates lying on one another, a good sealing action is achieved even with just a slight bearing pressure of the ball on the sealing edge. In order to free the at least one flow channel, the invention provides that the ball can be moved to a release position, substantially in a direction transverse to the longitudinal direction of the flow channel, this movement being effected by means of the actuating member being moved likewise in the direction transverse to the flow channel, which, in contrast to the ceramic plates of the known instrument, requires lower operating forces, because there is no real friction to be overcome for movement of the ball.

The use of a ball valve for a medical instrument is known per se from DE 28 00 607 A1. In this known surgical laparoscope, the ball valve is used to close the optic channel or instrument channel of a trocar sleeve which does not serve for irrigation or suction. In this known instrument, the ball is held by magnetic forces in a funnel-shaped recess of the trocar sleeve and, in order to free the optic channel or instrument channel, the ball is pushed from its seat by the inserted surgical optic or by an inserted instrument. Accordingly, in this known instrument, there is no active controlled actuation of the ball valve for opening or closing.

An elastic design of the ball advantageously contributes to an improved sealing action in relation to the sealing edge of the flow channel, because the ball, on account of its shape elasticity, can adapt snugly to the sealing edge of the flow channel, and any surface irregularities or rough surfaces of the ball or of the sealing edge of the flow channel cannot adversely affect the sealing action of the shut-off member.

For further improved handling of the instrument according to the invention, the actuating member has a press-button for operating the actuating member.

Further, the actuating member can be removed from the instrument body together with the ball.

The advantage of this measure is that, on the one hand, the ball can be replaced if it becomes worn and that, on the other hand, the shut-off member and the actuating member can be easily cleaned after removal from the instrument body. Particularly in the case where the at least one flow channel is a suction channel for aspiration of fluids, tissue remnants and the like, impurities can accumulate in the area of the shut-off member and these are much easier to clear because of the actuating member and the ball being removable. In this way, the instrument according to the invention also satisfies the strict requirements generally placed on medical instruments in respect of the disinfection and cleaning of such instruments.

In a preferred embodiment of the invention, the ball is arranged upstream of the sealing edge of the flow channel.

This measure has the advantage that in the case where the at least one flow channel is a suction channel, the ball can be pressed against the sealing edge of the flow channel exclusively as a result of the suction pressure, and in the case where the at least one flow channel is an irrigation channel, the ball can be pressed against the sealing edge of the flow channel exclusively by the irrigation pressure. Structurally elaborate means for pressing the ball onto the sealing edge of the flow channel, for example springs or the like, are advantageously not necessary in this construction. Moreover, this measure ensures that the pressing of the ball on the sealing edge is even increased as the suction or irrigation pressure rises, as a result of which the locking force required for securely shutting off the flow channel is automatically set.

In a further preferred embodiment, the ball is arranged in a receiving seat of the actuating member, in which receiving seat the ball has a mobility in the longitudinal direction of the flow channel.

The advantage here is that, during its movement from the closure position to the release position and vice versa, the ball can be more easily moved past the sealing edge of the flow channel on account of its axial mobility. This measure thus advantageously contributes to the actuating member being able to be operated with much less operating force.

In a further preferred embodiment, the ball is mounted so as to be rotatable substantially about its center in the receiving seat.

This measure also advantageously contributes to reducing the operating force of the actuating member, because the ball, by virtue of this design, can roll along the sealing edge of the flow channel when it is moved from the closure position to the release position and vice versa.

In a further preferred embodiment, the mobility of the ball in the receiving seat is limited in the longitudinal direction of the flow channel counter to the direction of flow of the fluid.

While the mobility of the ball in the longitudinal direction of the flow channel in the direction of flow of the fluid is limited by the sealing edge of the flow channel, this measure has the advantage that, when the instrument is in a state in which there is no fluid pressure, for example no suction pressure or irrigation pressure, the ball in the instrument body cannot move away from the actuating member.

In a further preferred embodiment, the ball in the receiving seat is held substantially immovably in the direction transverse to the flow channel.

The advantage here is that, at least in the closure position, the ball assumes the centered position, relative to the sealing edge of the flow channel, which is favorable for achieving a good sealing action.

In a further preferred embodiment, the actuating member is prestressed into the closure position or the release position of the ball.

This prestressing of the actuating member has the advantage that at least one of the two operating positions of the ball, i.e. the closure position or the release position, is automatically adopted when the actuating member is let go, which improves the user-friendliness of the instrument according to the invention. The prestressing can advantageously be effected by means of a spring provided on the actuating member.

In a further preferred embodiment, provision is made for a locking mechanism in the form of a bayonet catch to be present on the actuating member and on the instrument body for the purpose of locking the actuating member on the instrument body.

In this way, the actuating member and the ball can be removed in an easily manageable way, as a result of which the instrument can be dismantled and put together again particularly quickly, so that the instrument can be easily and quickly made ready for cleaning.

In a further preferred embodiment, in order to lock and unlock the locking mechanism, a lever is provided which can be pivoted about a longitudinal axis of the actuating member.

This measure results in even easier and quicker removal and fitting of the actuating member and of the ball.

In a further preferred embodiment, at least two flow channels are present in the instrument body, and each flow channel is assigned a shut-off member and an actuating member.

With this configuration, a combined suction and irrigation instrument can be realized in which, by easy actuation of the respective actuating member, it is possible to switch between the functions of irrigation, suction, and shutting-off both of the suction channel and also of the irrigation channel.

In a further preferred embodiment, as an alternative to the abovementioned freely rotatable mounting of the ball in the receiving seat of the actuating member, provision is made for the ball to be prestressed in the direction toward the sealing edge of the flow channel.

This measure is particularly advantageous if there is a low pressure or a low pressure gradient in the flow channel, since the ball is pressed onto the sealing edge by the prestressing, as a result of which a sufficient sealing action of the ball on the sealing edge of the flow channel is achieved.

Further advantages and features will become evident from the following description and from the attached drawing.

It will be appreciated that the aforementioned features, and those features still to be explained below, can be used not only in the stated combination, but also in other combinations or in isolation, without departing from the scope of the present invention.

BRIEF DESCRIPTION OF THE DRAWINGS

Illustrative embodiments of the invention are shown in the drawings and are described in more detail below with reference to said drawing, in which:

FIG. 4 shows a view of the instrument comparable to FIG. 1, with removed shut-off members and actuating members in an exploded view; and FIG. 5 shows an extremely diagrammatic partial representation of the actuating member and the ball in a slightly modified embodiment.

DETAILED DESCRIPTION OF PREFERRED EMBODIMENTS

FIGS. 1 through 4 show a medical instrument which is designated generally by reference number 10 and which, in the illustrative embodiment shown, can be used both for irrigation and also for suction.

Figure 1:
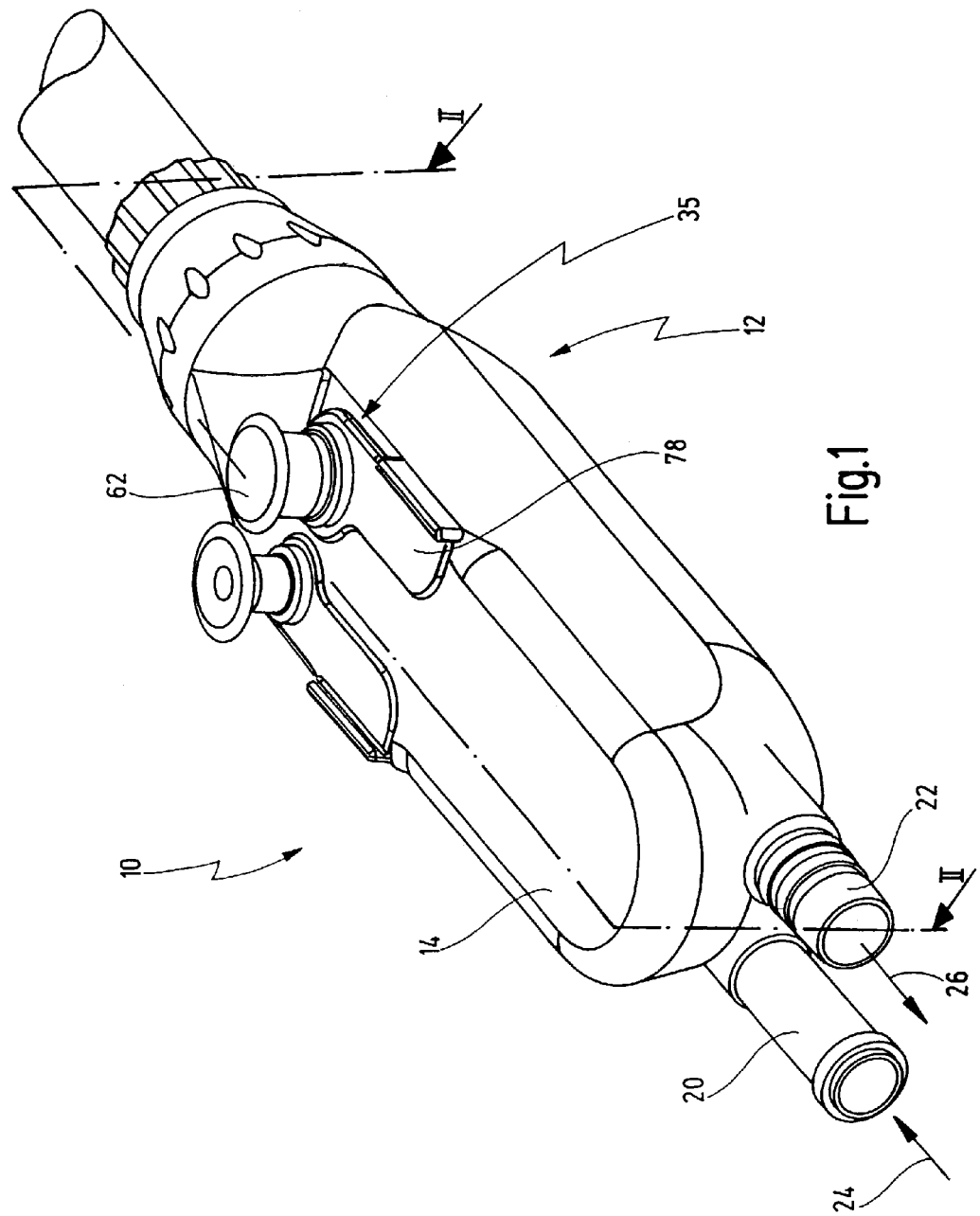
FIG. 1 shows a perspective overall view of a medical instrument for irrigation and suction, a shaft of the instrument being shown only in part.

The instrument 10 has generally an instrument body 12 which comprises a handgrip 14 and a shaft 16, only indicated in FIG. 1. The handgrip 14 is substantially rod-shaped. The shaft 16 can be connected to the handgrip 14 via a receiver 17 (FIGS. 2 and 3) at the distal end of the handgrip 14 and can be secured by means of a fastening screw 18.

An irrigation attachment piece 20 and a suction attachment piece 22, lying next to one another in a plan view, are arranged at the proximal end of the handgrip 14.

By means of an irrigation tube (not shown) which is connected to the irrigation attachment piece 20, and by means of a suction tube (not shown) which is connected to the suction attachment piece 22, the instrument 10 can be connected to a suction and irrigation source (not shown). A fluid, for example irrigation fluid, coming from the irrigation source is delivered to the irrigation attachment piece 20 in accordance with an arrow 24 in FIG. 1, and an underpressure is applied to the instrument 10 at the suction attachment piece 22 in accordance with an arrow 26 in FIG. 1.

Figure 2:
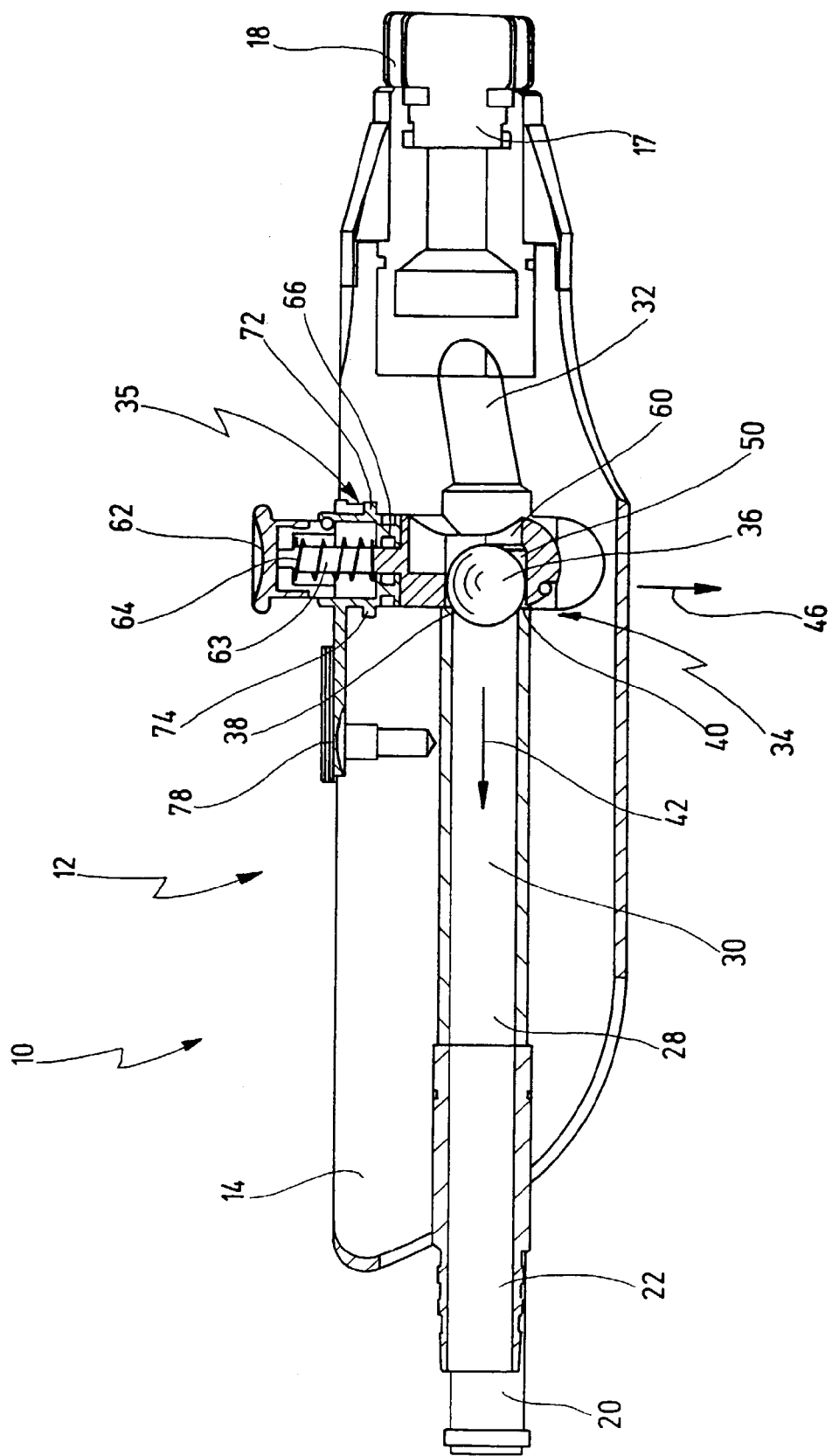
FIG. 2 shows a cross section through the instrument in FIG. 1 along the line II—II in FIG. 1, with a shut-off member of the instrument being shown in its closure position.
Figure 3:
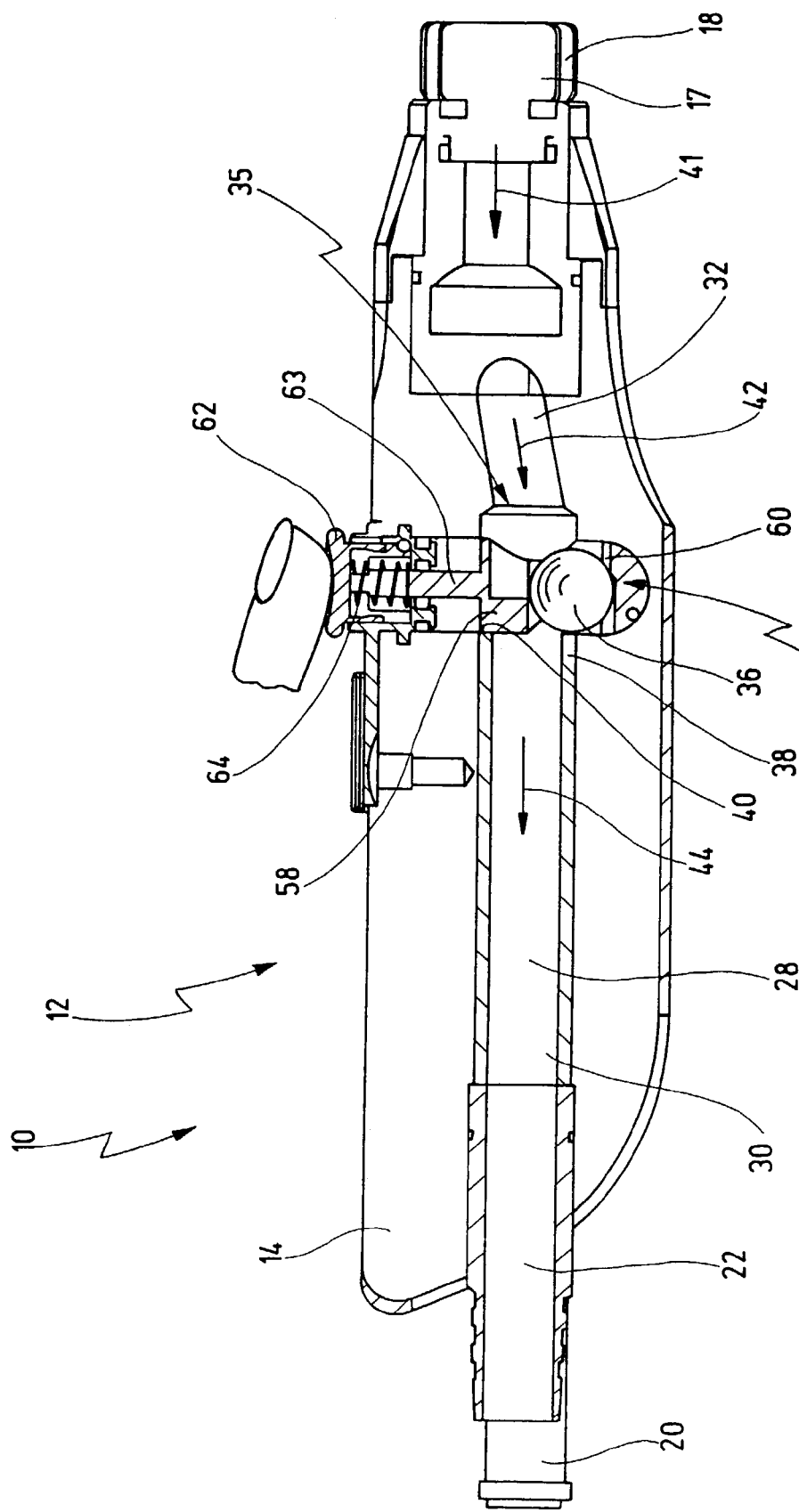
FIG. 3 shows a view of the instrument corresponding to FIG. 2, with the shut-off member being shown in its release position.

Starting from the irrigation attachment piece 20 and from the suction attachment piece 22, a flow channel for the passage of a fluid extends in each case through the instrument 10, i.e. starting from the irrigation attachment piece 20, a flow channel (not shown in detail) serving as irrigation channel extends through the instrument body 12, and, starting from the suction attachment piece 22, a flow channel 28 serving as suction channel extends through the instrument body 12. The longitudinal section according to FIGS. 2 and 3 is taken through the flow channel 28, while the irrigation channel (not shown in FIGS. 2 and 3) extends separately from the flow channel 28 and parallel to it.

The flow channel 28 (the same applies to the further flow channel for irrigation) extends right through the handgrip 14 to the shaft 16 and continues through the shaft 16 as far as the distal end thereof (not shown). In the shaft 16, the flow channels can continue to extend separately from one another, although they can also be brought together in the shaft 16.

The following description is limited to describing the flow channel 28 (suction channel) and the elements 10 of the instrument which cooperate with it. The further flow channel (irrigation channel) which is not shown in detail, and the elements which cooperate with it, do not differ structurally from the flow channel 28, and from the elements cooperating with it, unless otherwise stated in the description below.

A shut-off member 34 for alternately shutting off and freeing the flow channel 28 is coupled into the flow channel 28, and this shut-off member 34 will be described in more detail below. The shut-off member 34 is in this case arranged in the handgrip 14 of the instrument 10 and, for the purpose of simplifying the description, divides the flow channel 28 into a proximal portion 30 and a distal portion 32.

The shut-off member 34 can be actuated via an actuating member 35, which will also be described in more detail below, the shut-off member 34 being movable between a closure position (FIG. 2) and a release position (FIG. 3).

The shut-off member 34 is designed as a ball 36 and is arranged adjacent to a distal end 38 of the proximal portion 30 of the flow channel 28.

At the distal end 38 of its proximal portion 30, the flow channel 28 has a sealing edge 40 which is an end-edge of the proximal portion 30 and on which the ball 36 lies sealingly in its closure position according to FIG. 2, so that the ball 36 closes off the internal cross section of the flow channel 28. For this purpose, at least the distal end 38 or sealing edge 40 is round in cross section, so that the ball 36 lies sealingly on the sealing edge 40 of the flow channel 28 along a closed line of a circle or a closed circular ring. The ball 36 correspondingly has a diameter which is greater than the internal diameter of the flow channel 28.

In the closure position according to FIG. 2, the ball 36 is pressed against the sealing edge 40 of the flow channel 28 exclusively by the suction pressure or flow pressure prevailing in the flow channel 28 according to an arrow 42. This is made possible by the fact that the ball 36 is arranged upstream of the sealing edge 40 of the flow channel 28 in relation to the direction of flow through the flow channel 28 or the direction of the pressure gradient of the fluid.

In the closure position of the ball 36 shown in FIG. 2, no fluid can thus pass through the flow channel 28, i.e. the suction or fluid stream through the flow channel 28 is interrupted in this closure position. To free the flow channel 28, in the present case in order to aspirate fluids, tissue remnants and the like through the flow channel 28 according to the arrows 41, 42 and 44, the ball 36 can be moved, from the closure position shown in FIG. 2 to a release position according to FIG. 3, substantially in a direction transverse to the longitudinal direction of the flow channel 28, i.e. in the direction of an arrow 46.

This movement of the ball 36 from the closure position to the release position is actively effected by means of the actuating member 35, as is also the reverse movement of the ball 36 from the release position in FIG. 3 to the closure position in FIG. 2. For this purpose, the actuating member 35 is movable in a direction transverse to the flow channel 28.

The actuating member 35 is designed in the form of a slide which has a receiving seat 50 for the ball 36.

According to FIGS. 2 and 4, the receiving seat 50 is designed in the form of a cage by means of retention elements 52 and 54 which enclose the ball 36 from in front and behind in the actuation direction, or from above and below in FIGS. 2 and 4, and by means of retention elements 56 and 58 which are situated to the side of the actuation direction and enclose the ball substantially laterally. In this way, the ball 36 is held immovably in the receiving seat 50 in directions which are directed transverse to the flow channel 28. In the area of the retention element 52, the lateral retention elements 56 and 58 and the retention element 52 leave an opening 59 free for the passage of the fluid.

In the receiving seat 50 of the actuating member 35, the ball 36 has, in the longitudinal direction of the flow channel 28, a mobility which is limited at the distal end 38 of the proximal portion 30 of the flow channel 28 by the sealing edge 40 and is limited in the opposite direction by a limit stop 60.

In addition, the ball 36 is mounted in the receiving seat 50 so as to be rotatable, substantially about its center.

Because of the mobility of the ball 36 in the longitudinal direction of the flow channel 28, the ball 36, in the movement from the closure position according to FIG. 2 into the release position according to FIG. 3 and vice versa, moves easily around the lower area of the sealing edge 40 of the flow channel 28, without high operating forces having to be applied. Because of the rotatable mounting of the ball 36 in the receiving seat 50 of the actuating member 35, the ball 36 additionally rolls on the front area, or in FIGS. 2 and 3 the lower area, of the sealing edge 40, as a result of which the frictional forces during movement of the ball 36 from the closure position to the release position and vice versa and still further reduced.

The ball 36 is additionally elastic in shape, so that, in the closure position according to FIG. 2, it adapts snugly to the sealing edge 40 of the flow channel 28 to afford a particularly good sealing action.

The actuating member 35 also has a press-button 62 which is connected to the receiving seat 50 via a ram 63 for the purpose of moving the ball 36. The press-button 62 can be comfortably operated with the thumb of the hand which is holding the handgrip 14.

The actuating member 35 is prestressed by means of a spring 64 into the closure position of the ball 36. The spring 64 is supported between the press-button 62 and a securing part 66 of the actuating member 84 fixed in relation to the instrument body 12, the press-button 62 being movable together with the ram 63 relative to the securing part 66.

In the closure position of the ball 36 shown in FIG. 2, the suction stream on the flow channel 28 is interrupted. If the instrument 10 is now to be used for aspiration, the press-button 62 is pressed down according to FIG. 3, by which means the ball 36 is moved to the release position in FIG. 3 by means of rolling or superposed rolling and sliding on the front area of the sealing edge 40 in the direction of actuation, or in FIGS. 2 and 3 on the lower area of the sealing edge 40, the ball 36 also moving slightly axially in the distal direction.

The actuating member 35 with the ball 36 is received in the instrument body 12, i.e. in the present case in the handgrip 14, in an opening 68 in the form of a blind hole in the handgrip 14. The actuating member 35 can in this case be removed together with the ball 36 from the instrument body 12, i.e. in the present case from the handgrip 14, as is shown in FIG. 4.

In the state of removal from the instrument body 12 as shown in FIG. 4, the ball 36 can further be removed from the actuating member 35, for example if the ball 36 is to be replaced because of wear. For this purpose, the ball 36 can be removed from the retention elements 52, 54, 56 and 58 in the direction of an arrow 70.

To lock and unlock the actuating member 35 on the instrument body 12, a locking mechanism is provided in the form of a bayonet catch which comprises a groove 72 on the instrument body 12 and a corresponding projection 74 on the actuating member 35. For locking and unlocking, a lever 78 is also provided which can be pivoted about a longitudinal axis 76 and which, in the locking position according to FIG. 1, is arranged approximately in the longitudinal direction of the instrument 10 and, in the unlocked position, is pivoted through about 90° from this position, as is shown in FIG. 4.

As has already been mentioned, in addition to the flow channel 28 designed as a suction channel, the instrument 10 also has a second flow channel which is parallel thereto and which is designed as an irrigation channel. This irrigation channel is correspondingly assigned a shut-off member 80 in the form of a ball (FIG. 4) and an actuating member 84. The configuration of the actuating member 84 in combination with the ball 82 corresponds to the configuration of the actuating member 84 in combination with the ball 36. However, since the direction of flow in the irrigation channel is opposite to the direction of flow in the suction channel, the ball 82 is arranged at a proximal end (not shown in detail) of a distal portion (not shown in detail) of the irrigation channel, on which in turn a sealing edge is provided on which the ball 82 lies sealingly in the closure position, and specifically as a result of the irrigation pressure directed from proximal to distal in the irrigation channel.

FIG. 5 shows a diagrammatic representation of an illustrative embodiment which is slightly modified in relation to the above-described illustrative embodiment and in which the ball 36 is not mounted so as to be freely rotatable in the receiving seat 50 of the actuating member 35, but is instead fastened on the actuating member by a kind of tongue or lever 90. It will be appreciated that the fastening is releasable so as to be able to remove the ball 36 from the actuating member.

The lever or tongue 90 prestress the ball 36 in the direction of the sealing edge 40 of the flow channel 28, as a result of which the ball 36 is pressed against this edge in the closure position. In this way, the prestressing ensures a sufficient sealing action of the ball 36 even when the flow pressure, the pressure gradient or the pressure/volume flow ratio in the flow channel 28 is low.

The invention claimed is:

1. A medical instrument capable of irrigation and/or suction with a fluid, comprising:
   an instrument body in which at least one flow channel is present having an internal cross section for the passage of a fluid, said flow channel extending in a longitudinal direction;
   at least one shut-off member configured as a ball which is movable between a closure position where said ball lies sealingly on a sealing edge of said at least one flow channel so that it closes off said internal cross section of said flow channel, and a release position where said ball frees said flow channel, said ball being elastic in order to facilitate sealing of said flow channel by said elastic ball when said ball is in said closure position;
   at least one actuating member for moving said ball between said closure position and said release position, said actuating member having a press-button for operating said actuating member, and
   wherein said ball and said actuating member are movable between said closure position and said release position substantially in a direction transverse to said longitudinal direction of said flow channel, and wherein said actuating member is configured to remove from said instrument body together with said ball as a unit.

2. The instrument of claim 1, wherein said ball is arranged upstream of said sealing edge of said flow channel.

3. The instrument of claim 1, wherein said actuating member is prestressed into said closure position or said release position of said ball.

4. The instrument of claim 1, wherein a locking mechanism in the form of a bayonet catch is present on said actuating member and on said instrument body for the purpose of locking said actuating member on said instrument body.

5. The instrument of claim 1, wherein said ball is prestressed in a direction toward said sealing edge of said flow channel.

6. The instrument of claim 1, wherein said press-button is connected to the ball via a ram, and the actuating member is prestressed by means of a spring supported between said press-button and a securing part of said actuating member fixed in relation to said instrument body, wherein said press-button is movable together with said ram relative to said securing part.

7. A medical instrument capable of irrigation and/or suction with a fluid, comprising:
    an instrument body in which at least one flow channel is present—having an internal cross section for the passage of a fluid, said flow channel extending in a longitudinal direction;
    at least one shut-off member configured as a ball which is movable between a closure position where said ball lies sealingly on a sealing edge of said at least one flow channel so that it closes off said internal cross section of said flow channel, and a release position where said ball frees said flow channel, said ball being elastic;
    at least one actuating member for moving said ball between said closure position and said release position, said actuating member having a press-button for operating said actuating member;
    wherein said ball and said actuating member are movable between said closure position and said release position substantially in a direction transverse to said longitudinal direction of said flow channel, and wherein said actuating member can be removed from said instrument body together with said ball as a unit, and
    wherein said ball is arranged in a receiving seat of said actuating member, in which receiving seat said ball has a mobility in said longitudinal direction of said flow channel.

8. The instrument of claim 7, wherein said ball is mounted so as to be rotatable substantially about its center in said receiving seat.

9. The instrument of claim 7, wherein said mobility of said ball in said receiving seat counter to the direction of flow of said fluid is limited.

10. The instrument of claim 7, wherein said ball in said receiving seat is held substantially immovably in said direction transverse to said flow channel.

11. A medical instrument capable of irrigation and/or suction with a fluid, comprising:
    an instrument body in which at least one flow channel is present—having an internal cross section for the passage of a fluid, said flow channel extending in a longitudinal direction;
    at least one shut-off member configured as a ball which is movable between a closure position where said ball lies sealingly on a sealing edge of said at least one flow channel so that it closes off said internal cross section of said flow channel, and a release position where said ball frees said flow channel, said ball being elastic;
    at least one actuating member for moving said ball between said closure position and said release position, said actuating member having a press-button for operating said actuating member;
    wherein said ball and said actuating member are movable between said closure position and said release position substantially in a direction transverse to said longitudinal direction of said flow channel, and wherein said actuating member can be removed from said instrument body together with said ball;
    wherein a locking mechanism in the form of a bayonet catch is present on said actuating member and on said instrument body for the purpose of locking said actuating member on said instrument body, and
    wherein, in order to lock and unlock said locking mechanism, a lever is provided which can be pivoted about a longitudinal axis of said actuating member.

12. A medical instrument capable of irrigation and/or suction with a fluid, comprising:
    an instrument body in which at least one flow channel is present—having an internal cross section for the passage of a fluid, said flow channel extending in a longitudinal direction;
    at least one shut-off member configured as a ball which is movable between a closure position where said ball lies sealingly on a sealing edge of said at least one flow channel so that it closes off said internal cross section of said flow channel, and a release position where said ball frees said flow channel, said ball being elastic;
    at least one actuating member for moving said ball between said closure position and said release position, said actuating member having a press-button for operating said actuating member;
    wherein said ball and said actuating member are movable between said closure position and said release position substantially in a direction transverse to said longitudinal direction of said flow channel, and wherein said actuating member can be removed from said instrument body together with said ball, and
    wherein at least two flow channels are present in the instrument body, and each flow channel is assigned a shut-off member and an actuating member.

* * * * *